United States Patent [19]

Yasuda et al.

[11] 4,418,221

[45] Nov. 29, 1983

[54] PROCESS FOR TREATING AQUEOUS SOLUTIONS CONTAINING PHENOLS

[75] Inventors: Sinichi Yasuda, Otsu; Takayuki Kurohara, Hirakata; Akira Taguro, Osaka, all of Japan

[73] Assignee: Koei Chemical Co., Ltd., Osaka, Japan

[21] Appl. No.: 357,466

[22] Filed: Mar. 12, 1982

[30] Foreign Application Priority Data

Mar. 19, 1981 [JP]  Japan ............................... 56-41124

[51] Int. Cl.³ .................. C07C 37/68; C07C 37/84
[52] U.S. Cl. ........................... 568/757; 568/749; 568/750
[58] Field of Search ....................... 568/749, 757

[56] References Cited

U.S. PATENT DOCUMENTS

| | | | |
|---|---|---|---|
| 2,321,036 | 6/1943 | Luten, Jr. et al. | 568/757 |
| 2,432,062 | 12/1947 | Cislak et al. | 568/757 |
| 2,432,063 | 12/1947 | Cislak et al. | 568/757 |
| 2,474,028 | 6/1949 | Berger | 568/757 |
| 2,526,807 | 10/1950 | Cislak et al. | 568/757 |
| 2,803,375 | 10/1957 | Manka | 568/757 |
| 2,812,305 | 11/1957 | Manka | 568/757 |

FOREIGN PATENT DOCUMENTS

| | | | |
|---|---|---|---|
| 39-21352 | 9/1964 | Japan | 568/757 |
| 876452 | 9/1961 | United Kingdom | 568/749 |
| 908079 | 10/1962 | United Kingdom | 568/757 |

*Primary Examiner*—Werren B. Lone
*Attorney, Agent, or Firm*—Stevens, Davis, Miller & Mosher

[57] ABSTRACT

In removing a phenol from an aqueous solution containing the phenol, the phenol could be extracted quite effectively regardless of concentration of the phenol by using, as extracting solvent, a nitrogen-containing heterocyclic compound having a total carbon number of 9 or more either alone or in the state of a dilution with a water-insoluble organic solvent.

11 Claims, No Drawings

PROCESS FOR TREATING AQUEOUS SOLUTIONS CONTAINING PHENOLS

BACKGROUND OF THE INVENTION

1. Field of the Invention

This invention relates to a process for treating aqueous solutions containing phenols.

2. Description of the Prior Art

In Japan, some of the phenols are designated as special chemical substances by the Law of Labor Safety and Hygiene, and the content of phenols in waste waters is strictly regulated from the viewpoint of environmental protection. Accordingly, a variety of processes have been devised for removing phenols. However, all these processes have some faults.

As one of these processes, the activated sludge process can be referred to. This process is employed as a process for removing phenols from aqueous solutions containing relatively low concentration of phenols. However, it has a problem that it cannot be employed when the concentration of phenols is high. Also, the post-treatment of sludge is troublesome. A further fault of this process consists in that the phenols cannot be reused as a resource.

As another process, there has been proposed a process of extracting phenols from phenol-containing aqueous solutions by using, as an extracting solvent, an organic solvent such as hydrocarbons (for example, benzene and the like), ethers (for example, isopropyl ether) or alcohols (for example, octanol). However, if a hydrocarbon is used as the extracting solvent, the efficiency of extraction is quite low. If an alcohol such as octanol or an alcohol diluted with hydrocarbon is used as extracting solvent, a considerably long period of time is necessary for separating the extract solution from the water treated, even though their ability of extraction is fairly high. Further, this process has a problem that, when the extracted phenols are released from the extract solution by the use of an alkali, a loss of the alkali occurs due to its transfer into extracting solvent and the extractant must be washed with water which complicates the procedure. Having these many faults, the process of using hydrocarbon or alcohol as extracting solvent is difficult to employ industrially.

When an extraction process is to be adopted, therefore, it is usual to use an ether such as isopropyl ether as the extracting solvent, as is mentioned in British Pat. No. 876,452. However, ethers are quite difficult to handle in that they form an explosive peroxide upon contact with air and have a low flash point. Further, when the phenols extracted into the ether, used as extracting solvent, are released with an alkali, separation of the liquid phases is quite slow. Further, when the phenols extracted into the extracting solvent are recovered by distillation at elevated temperature, ethers have a lower boiling point than phenols, so that it is necessary to distil out the ether first and thereafter to recover the phenols again by distillation. Such a process cannot be said to be advantageous industrially because it requires heat energy for distilling the ether.

In U.S. Pat. No. 2,812,305 there is proposed a process for removing phenols by using a mixture of aromatic hydrocarbon and 5-ethyl-2-methylpyridine as an extracting solvent. However, this process has low efficiency of extraction. In addition, this process has various faults. For example, 5-ethyl-2-methylpyridine has a boiling point of 177.8° C./747 mm Hg which is very close to the boiling point of phenol (181.75° C./760 mm Hg), so that it is quite difficult industrially to separate phenol from the extracting solvent by the distillation of the phenol-containing extract solution. Even if it is possible to separate them by distillation, phenol must be recovered by distillation after 5-ethyl-2-methylpyridine has distilled out because 5-ethyl-2-methylpyridine has a lower boiling point than phenol, and a large quantity of steam is necessary for distilling 5-ethyl-2-methylpyridine.

SUMMARY OF THE INVENTION

It is an object of this invention to provide a novel process for treating aqueous solutions containing phenols by which the above-mentioned faults of prior techniques can be overcome.

Other and further objects, features and advantages of this invention will appear more fully from the following description.

The present inventors conducted studies with the aim of achieving these objects to find out that, in extracting and removing phenols from phenol-containing aqueous solutions, the phenols can be extracted quite effectively without any relation to the concentration of the phenols by using, as an extracting solvent, a nitrogen-containing heterocyclic compound having a total carbon number of 9 or more, either alone or diluted with a water-insoluble organic solvent. According to this invention, the phenol concentration in phenol-containing aqueous solutions can easily be decreased to a value not exceeding the environmental standard and, at this time, the phenols can be extracted more speedily than with hitherto known extracting solvents and the separation between the extract solution and treated water is very good.

DETAILED DESCRIPTION OF THE INVENTION

According to one preferable embodiment of this invention, an extracting solvent having a higher boiling point than the boiling point of phenol is used, and the extract solution which has contained phenol from phenol-containing aqueous solution is heated to a temperature higher than the boiling point of the phenol under ordinary or reduced pressure, by which only the phenol can be distilled out from the extract solution and can be recovered easily. Otherwise, it is also possible to recover the phenol in the state of a very highly concentrated aqueous solution of alkali phenolate by contacting the extract solution with an aqueous solution of alkali. At this time, unlike the case of hitherto known extracting solvent, the aqueous alkali solution does not transfer into extracting solvent and the phenol can be released from the extract solution quite readily.

The phenol thus recovered has a high purity, so that it can be reused as a phenol as it is. Of course, the extracting solvent from which the phenol has been removed can be used as an extracting solvent for the next run, as it is. Accordingly, the process of this invention can be said to be an industrially and economically quite excellent process for removing phenols from phenol-containing aqueous solutions and for recovering the phenols. In addition, another advantage of the treating process of this invention resides in that it forms no sludge, unlike the activated sludge process, which is desirable from the viewpoint of industrial wastes. As above, it is needless to say that this invention is quite effectively applicable to diluted waste waters containing phenols, and it is also needless to say that this invention can be incorporated into general processes using or producing phenols as a means for quite effectively recovering phenols from aqueous solutions containing various concentrations of phenols.

The above-mentioned marked effect of the extracting solvent used in this invention is considered owing to that it not only acts as an extracting solvent but also it partially takes part in a chemical combination with phenols. Accordingly, the intention of this invention resides in extracting phenols with a very high efficiency without being greatly affected by the concentration of the phenols. Further, in distilling the phenols at elevated temperatures, the phenols chemically combined with extracting solvent can be dissociated at an appropriate temperature.

As said nitrogen-containing heterocyclic compounds having a total carbon number of 9 or more (the term "total carbon number" means the total number of carbon atoms which the compound has), compounds having the skeletal structure of pyridine, compounds having the skeletal structure of piperidine, compounds having the skeletal structure of pyrazine, compounds having the skeletal structure of piperazine, compounds having the skeletal structure of carbazole, compounds having the skeletal structure of triazine, compounds having the skeletal structure of quinoline, compounds having the skeletal structure of isoquinoline, compounds having the skeletal structure of pyrrolidine and compounds having the skeletal structure of pyrimidine can be mentioned to.

As said compounds having the skeletal structure of pyridine, there can be mentioned to alkylpyridines such as nonylpyridine and the like; alkenylpyridines such as 4-(butenylpentenyl)-pyridine and the like; aralkylpyridines such as benzylpyridine, phenylpropylpyridine and the like; dipyridyls such as 4,4'-dipyridyl, 4,4'-dimethyl-2,2-dipyridyl and the like; dipyridylalkanes such as 1,3-di-(4-pyridyl)-propane and the like.

As said compounds having the skeletal structure of piperidine, there can be mentioned to aralkylpiperidines such as benzylpiperidine and the like, as well as 1,3-di-(4-piperidyl)-propane, alkylpiperidines and the like.

As said compounds having the skeletal structure of pyrazine and compounds having the skeletal structure of piperazine, there can be mentioned to alkylpyrazines, phenylpyrazine, alkylpiperazines, phenylpiperazine and the like.

As said compounds having the skeletal structure of quinoline, there can be mentioned to quinoline, quinaldine and the like. As said compounds having the skeletal structure of isoquinoline, there can be mentioned to isoquinoline, 2-ethylisoquinoline and the like.

As said compounds having the skeletal structure of imidazole, there can be mentioned to alkylimidazoles, phenylimidazole, benzylimidazole and the like.

As said compounds having the skeletal structure of carbazole, there can be mentioned to carbazole and the like.

As said compounds having the skeletal structure of triazine, there can be mentioned to 4-pyridyltriazine, 2,4,6-tri-(4-pyridyl)-s-triazine and the like.

As said compounds having the skeletal structure of pyrrolidine, there can be mentioned to phenylpyrrolidine and the like.

As said compounds having the skeletal structure of pyrimidine, there can be mentioned to phenylpyrimidine and the like.

In this invention, it is also allowable to use the extracting solvent in the state of dilution with a water-insoluble organic solvent.

When the nitrogen-containing heterocyclic compound is diluted with a water-soluble organic solvent, the proportion of dilution may be so selected that the amount of nitrogen-containing heterocyclic compound comes to 5-95%, preferably 20-95% and more preferably 40-80% based on the amount of water-insoluble organic solvent. As examples of said water-insoluble organic solvent, the following can be referred to: aromatic hydrocarbons such as benzene, toluene, xylene, dodecylbenzene, p-cymene and the like; aliphatic hydrocarbons such as octane, isooctane, n-decane and the like; higher alcohols having 5 or more carbon atoms such as hexanol, octanol, dodecyl alcohol, lauryl alcohol and the like; organic carboxylic esters such as ethyl propionate, butyl acetate and the like; ketones such as methyl isopropyl ketone, acetophenone and the like; alicyclic hydrocarbons such as cyclohexane, methylcyclohexane and the like; ethers such as n-butyl ether, diisoamyl ether and the like; and their mixtures. However, this invention is not limited by the above-mentioned solvents. Said water-insoluble organic solvent may be selected appropriately in accordance with the kind of the nitrogen-containing heterocyclic compound.

Next, the phenols are extracted from the phenol-containing aqueous solution with the extracting solvent of this invention, and the extract solution thus obtained is distilled under ordinary or reduced pressure. By this procedure, the phenols can be removed and recovered. In this case, the temperature of the distilling may be any temperature as long as it is not lower than the temperature at which the phenols chemically combined with extracting solvent can be thermally dissociated into free phenols under ordinary or reduced pressure. As the method for recovering phenols with distilling, a method using simple a distillation tower or rectifying tower is usually preferable. A procedure which comprises distilling the extract solution to distil out only phenols under ordinary or reduced pressure and thereby separate them from extracting solvent is usually preferable from the economical point of view.

The phenols recovered in the above-mentioned manner have a very high purity so that they can be reused as they are, as a phenol. At the same time, the phenols can be recovered almost completely from the extract solution with a high efficiency. Accordingly, the extracting solvent from which the phenols have been released can directly be reused as the extracting solvent for the next run, so that only minor losses of extracting solvent take place.

On the other hand, it is also possible to recover the phenols extracted into the extracting solvent of this invention by releasing them in the form of an aqueous solution of alkali phenolate by the use of an aqueous alkali solution. In this case, a stoichiometric amount of alkali is enough to release the phenols. An aqueous alkali solution containing phenolate can also be used as the releasing agent. If a highly concentrated aqueous alkali solution containing an excessive quantity, to the phenols present in the extract solution, of alkali is circulatingly used as the releasing agent, a solution of phenolate having a high concentration can be recovered, which is quite advantageous when phenols are to be recovered from phenolate solution. In this case, the release of phenols from extract solution takes place completely regardless of the concentration of phenolate, so long as the aqueous alkali solution remains alkaline. Of course, the extracting solvent from which phenols have been released can be used repeatedly as it is, in the next extraction step.

As the phenol-containing aqueous solution to which this invention is applicable, there can be mentioned aqueous solutions containing at least one kind of phenolic compound such as phenol, cresols, xylenols, catechols, chlorophenols, nitrophenols and the like. More concretely, there can be mentioned the phenol-containing aqueous solution formed at the time of producing phenol, the phenol-containing aqueous solution formed at the time of producing phenolic resins, the coke oven gas liquor formed at the time of producing cokes, the phenol-containing aqueous solution formed at the time of producing pharmaceuticals and pesticides, and so on. Among them, the phenol-containing aqueous solution formed at the time of producing phenolic resins contains methanol and formaldehyde in addition to phenol, and the coke oven gas liquor formed at the time of producing cokes contains thiocyan ion and complex cyan ion as main contaminative substances. Nevertheless, the extracting solvent of this invention can selectively extract only the phenols.

In practising this invention, the contact temperature at which phenols are extracted from phenol-containing aqueous solution with the extracting solvent of this invention may be any temperature as long as it is not higher than the boiling point of phenols and the boiling point of the extracting solvent of this invention. As the method of contact, any of batch process, mixer settler process and continuous extraction process using perforated tray tower, pulse tower, or the like can be employed.

Further, the practice of this invention requires no other chemicals, and the apparatus for it may be simpler and more small-sized than those in other processes, so that this invention is economical.

Next, this invention will be illustrated concretely with reference to examples and comparative example.

EXAMPLE 1

Fifty milliliters of an aqueous solution containing 990 ppm of reagent grade phenol and 20 ml of 4-(1-butenylpentenyl)-pyridine as an extracting solvent were introduced into a separating funnel and extraction was carried out by shaking the mixture for one minute, after which the mixture was separated into two phases immediately. Analysis revealed the phenol concentration in the raffinate of extraction to be 25 ppm. This means that extraction rate of phenol was 97.5% and therefore the distribution coefficient was 96.5.

Subsequently, the extract solution was back-extracted by shaking it with 50 ml of 4% (by weight) aqueous solution of NaOH for one minute. Thus, the phenol concentration (a value obtained by converting phenolate to phenol) in the aqueous NaOH solution was 953 ppm and the release rate was 98.8%.

EXAMPLE 2

Fifty milliliters of an aqueous solution containing 1% (by weight) of reagent grade o-cresol and 50 ml of a dodecyl alcohol solution containing 30% by weight of 1,3-di-(4-pyridyl)-propane as an extracting solvent were introduced into a separating funnel and extraction was carried out by shaking the mixture for one minute, after which the mixture was separated into two phases immediately. Analysis revealed the o-cresol concentration in the raffinate of extraction to be 130 ppm. This means that the extraction rate of o-cresol was 98.7% and therefore the distribution coefficient was 76.

Subsequently, the extract solution was back-extracted by shaking it with 50 ml of 4% (by weight) aqueous solution of NaOH for one minute. Thus, the o-cresol concentration (a value obtained by converting o-cresolate to o-cresol) in the aqueous NaOH solution was 9.690 ppm and the release rate was 98.2%.

EXAMPLE 3

Fifty milliliters of a waste water of phenolic resin factory containing 41,340 ppm of phenol and 50 ml of the extracting solvent shown in Table 1 were introduced into a separating funnel and extraction was carried out by shaking the mixture for 2 minutes. The mixture immediately separated into two phases. The phenol concentration in the raffinate of extraction was analyzed to reveal that phenol concentration, extraction rate and distribution coefficient were as shown in Table 1.

Subsequently, the extract solution was back-extracted by shaking it with 50 ml of 4% (by weight) aqueous solution of NaOH for 2 minutes. The phenol concentration (a value obtained by converting phenolate to phenol) in the aqueous NaOH solution was analyzed to reveal that phenol concentration and release rate were as shown in Table 1.

TABLE 1

| Extracting solvent | Composition of extracting solvent (ratio by wt.) | Phenol concentration in the raffinate of extraction (ppm) | Extraction rate (%) | Distribution coefficient K | Phenol concentration in the aqueous phase of back-extraction (ppm) | Release rate (%) |
|---|---|---|---|---|---|---|
| 4-Benzylpyridine | 40% | 827 | 98.0 | 49.0 | 39,700 | 99 |
| Benzene | 60% | | | | | |
| 4-(3-Phenylpropyl)-pyridine | 100% | 744 | 98.2 | 54.5 | 39,500 | 98 |
| 2,4,6-Tri-(4-pyridyl)-s-triazine | 30% | 579 | 98.6 | 70.3 | 40,180 | 100 |
| Dodecyl alcohol | 70% | | | | | |
| Quinoline | 40% | 500 | 98.8 | 81.7 | 40,430 | 99 |
| Mixed xylenes | 60% | | | | | |

COMPARATIVE EXAMPLE 1

Fifty milliliters of the waste water of phenolic resin factory used in Example 3 and 50 ml of the extracting solvent shown in Table 2 were shaken for 2 minutes for the sake of extraction. Phenol concentration in the raffinate of extraction was analyzed to reveal that phenol concentration, extraction rate and distribution coefficient were as shown in Table 2.

In the case of 2-ethylhexanol and oxocol, separation of the mixture was so slow that it separated into phases two hours after the extraction with shaking.

TABLE 2

| Extracting solvent | Phenol concentration in the raffinate of extraction (ppm) | Extraction rate (%) | Distribution coefficient K |
|---|---|---|---|
| Benzene | 11,780 | 71.5 | 2.5 |
| Octanol (2-Ethylhexanol) | 2,275 | 94.5 | 17.2 |
| p-Xylene | 15,590 | 62.3 | 1.6 |
| Isopropyl ether | 1,860 | 95.5 | 21.2 |
| Oxocol (Mixture of $C_{12}$-$C_{14}$ higher alcohols, manufactured by Nissan Chem. Ind.) | 2,480 | 94.0 | 16 |
| Kerosene | 35,550 | 14.0 | 0.2 |
| Dodecylbenzene (95 wt %) 5-ethyl-2-methylpyridine (5 wt %) | 3,720 | 91.0 | 10.1 |

EXAMPLE 4

Fifty milliliters of an aqueous solution containing a phenol compound, shown in Table 3, and 50 ml of a mixed xylene solution containing 40% by weight of 4-nonylpyridine as an extracting solvent were introduced into a separating funnel and extraction was carried out by shaking the mixture for 2 minutes. The concentration of the phenol compound in the raffinate of extraction was analyzed to reveal that phenol concentration, extraction rate and distribution coefficient were as shown in Table 3.

TABLE 3

| Kind of phenol compound | Phenol concentration before treatment (ppm) | Phenol concentration in the raffinate of extraction (ppm) | Extraction rate (%) | Distribution coefficient K |
|---|---|---|---|---|
| 2,5-Dimethylphenol | 9,500 | 120 | 98.7 | 78.1 |
| 2,4-Dichlorophenol | 2,900 | 35 | 98.8 | 81.8 |
| p-Nitrophenol | 4,800 | 55 | 98.9 | 86.3 |
| Catechol | 25,000 | 400 | 98.4 | 61.5 |

EXAMPLE 5

Two hundred milliliters of a waste water of phenolic resin factory containing 41,340 ppm of phenol and 200 ml of a mixed dodecylbenzene solution containing 30% by weight of 4-nonylpyridine as an extracting solvent were shaken for one minute and then immediately separated into layers. Then phenol concentration in the raffinate of extraction was analyzed. Subsequently, the raffinate was shaken with a fresh 200 ml portion of the above-mentioned extracting solvent for one minute for the sake of extraction, after which the phenol concentration in the raffinate of extraction was analyzed. This procedure was repeated three times in the total. Phenol concentration, extraction rate and distribution coefficient in the final raffinate were as shown in Table 4.

TABLE 4

| No. of extraction | Phenol concentration in the raffinate of extraction (ppm) | Extraction rate (%) | Distribution coefficient K |
|---|---|---|---|
| 1 | 660 | 98.4 | 61.6 |
| 2 | 5.4 | 99.2 | |
| 3 | 0 | 100 | |

EXAMPLE 6

Three hundred grams of a waste water of phenolic resin factory containing 63,000 ppm of phenol and 300 g of a mixed xylene solution containing 30% by weight of 4-(1-butenylpentenyl)-pyridine were introduced into a separating funnel and shaken for 2 minutes for the sake of extraction and then immediately separated into layers. The phenol concentration in the raffinate of extraction was 1,830 ppm. Subsequently, the extract solution was back-extracted by shaking it with 300 g of 20% (by weight) aqueous solution of NaOH for 2 minutes. The phenol concentration in the aqueous NaOH solution reached 5.47% by weight. Again, the extracting solvent from which phenol had been released was added to another 300 g portion of the same waste water of phenolic resin factory as above and shaken for the sake of extraction and the raffinate of extraction was separated, after which the extract solution was treated with the above-mentioned aqueous NaOH solution, containing 5.47% by weight of phenol, to release the phenol. The above-mentioned procedure was repeated 8 times in the total. Extraction rate and phenol concentration in the releasing NaOH solution after every run of extraction are shown in Table 5 and Table 6, respectively.

TABLE 5

| No. of extraction | Extraction rate (%) |
|---|---|
| 1 | 97.5 |
| 3 | 97.0 |
| 5 | 97.0 |
| 7 | 96.5 |

TABLE 5-continued

| No. of extraction | Extraction rate (%) |
|---|---|
| 8 | 96.0 |

TABLE 6

| No. of extraction | Phenol concentration in the releasing solution (% by wt.) |
|---|---|
| 1 | 5.47 |
| 3 | 14.7 |
| 5 | 22.0 |
| 7 | 27.0 |
| 8 | 30.47 |

[Step for recovering phenol]

To 399 g of the releasing solution obtained by repeating the above-mentioned procedure 8 times (containing 121 g of phenol) was added 60.5 g of concentrated sulfuric acid. The resulting oily phase was subjected to simple distillation under a reduced pressure of 100 mm Hg to obtain 100 g of phenol having a purity of 99.9% as measured by gas chromatography.

EXAMPLE 7

[Step of extraction]

Extraction was carried out by using a counter-current type of 3-stage glass-made mixer settler extractor. A waste water of phenolic resin factory containing 4.13% by weight of phenol was fed into the first tank at a rate of 1,200 ml/hour. From the third tank, a xylene solution containing 20% by weight of 4-nonylpyridine was let flow "counter-current"-wise at a rate of 1,200 ml/hour.

As the result, the raffinate of extraction was discharged at a rate of 1,140 ml/hour and its phenol concentration was 0.1 ppm, indicating that phenol had been extracted completely. The extract solution was discharged at a rate of 1,260 ml/hour, and its phenol concentration was 3.93% and its water content was 0.8%.

[Releasing step]

Three liters of the extract solution obtained in the step of extraction and 270 g of 20% (by weight) aqueous solution of NaOH were introduced into a separating funnel, and back-extraction was carried out. As the result, 390 g of a releasing solution was obtained. It contained 117 g of phenol, so that the release rate was 99.1%.

[Recovering step]

The releasing solution obtained in the releasing step, weighing 390 g, was neutralized with 68.5 g (1.05 times the theoretical amount) of concentrated sulfuric acid, and the mixture was separated into oily phase and aqueous phase. The oil thus obtained was introduced into a distillation flask and subjected to simple distillation under a reduced pressure of 100 mm Hg. As the result, 115 g of phenol was recovered. The phenol had a purity of 99.8% as measured by gas chromatography.

EXAMPLE 8

[Step of extraction-1]

Extraction was carried out by using a counter-current type of 3-stage glass-made mixer settler extractor. A waste water of phenolic resin factory containing 6.3% of phenol was fed into the first tank at a rate of 1,200 ml/hour. From the third tank, a diethyl phthalate solution containing 20% by weight of 4-nonylpyridine was let flow "counter-current"-wise at a rate of 480 ml/hour.

As the result, the raffinate of extraction was discharged at a rate of 1,128 ml/hour and its phenol concentration was 4.4 ppm, indicating that phenol had been extracted almost completely. The extract solution was discharged at a rate of 555 ml/hour, and its phenol concentration was 13% and its water content was 0.6%.

[Recovering step-1]

Ten liters of the extract solution obtained in the step of extraction (1,300 g of phenol and 30 g of water) was placed in a distillation flask having a capacity of 20 liters and subjected to simple distillation under a reduced pressure of 100 mm Hg. Thus, 1,280 g of phenol was recovered. The phenol had a purity of 99.8% as measured by gas chromatography. On the other hand, 8.7 liters of extracting solvent was recovered as the residue of distillation, which was reused as an extracting solvent for the next run.

[Step of extraction-2]

Under the same conditions as in Step of Extraction-1, extraction was carried out by using the extracting solvent recovered in the Recovering Step-1.

As the result, the raffinate of extraction was discharged at a rate of 1,126 ml/hour and its phenol concentration was 4.6 ppm, indicating that phenol had been extracted almost completely. The extract solution was discharged at a rate of 557 ml/hour, and its phenol concentrated was 12.8% and its water content was 0.7%.

[Recovering step-2]

Two liters of the extract solution obtained in Step of Extraction-2 (256 g of phenol and 7 g of water) was placed in a distillation flask having a capacity of 3 liters and subjected to simple distillation under a reduced pressure of 100 mm Hg. As the result, 246 g of phenol was recovered. It has a purity of 99.8% as measured by gas chromatography.

What is claimed is:

1. A process for treating an aqueous solution containing at least one phenol selected from the group consisting of phenol, cresols, xylenols, catechols, chlorophenols and nitrophenols, characterized by removing said phenol from said aqueous solution by extraction using an extracting solvent comprising a nitrogen-containing heterocyclic compound having a total carbon number of 9 or more, selected from the group consisting of a compound having the skeletal structure of pyridine, a compound having the skeletal structure of piperidine and a compound having the skeletal structure of triazine.

2. A process according to claim 1, wherein said extracting solvent is said nitrogen-containing heterocyclic compound having a total carbon number of 9 or more diluted with a water-insoluble organic solvent.

3. A process according to claim 1, wherein said heterocyclic compound is selected from the group consisting of an alkylpyridine, an alkenylpyridine, an aralkylpyridine, a dipyridyl and a dipyridylalkane.

4. A process according to claim 1, wherein said heterocyclic compound is selected from the group consisting of an alkylpiperidine and an aralkylpiperidine.

5. A process according to claim 1, wherein said heterocyclic compound is selected from the group consisting of 4-pyridyltriazine and 2,4,6-tri-(4-pyridyl)-s-triazine.

6. A process according to claim 2, wherein the content of the nitrogen-containing heterocyclic compound having a total carbon number of 9 or more diluted with water-insoluble organic solvent is 20-95% by weight based on said organic solvent.

7. A process according to claim 2, wherein said water-insoluble organic solvent is selected from the group consisting of hydrocarbons, organic carboxylic acids and higher alcohols having 5 or more carbon atoms.

8. A process according to claim 1, wherein said aqueous solution containing at least one phenol is selected from the group consisting of a coke oven gas liquor formed at the time of producing cokes, a phenol-containing aqueous solution formed at the time of producing phenolic resin, a phenol-containing aqueous solution formed at the time of producing a phenol, a phenol-containing aqueous solution formed at the time of producing pharmaceuticals and a phenol-containing aqueous solution formed at the time of producing pesticides.

9. A process according to claim 1 which additionally comprises recovering the phenol from the obtained phenol-containing extract solution by contacting the extract solution with an aqueous solution of alkali.

10. A process according to claim 1, which additionally comprises recovering the phenol from the obtained phenol-containing extract solution by distilling the extract solution.

11. A process according to claim 10, wherein the extracting solvent used is an extracting solvent whose boiling point is higher than that of the phenol to be extracted.

* * * * *